United States Patent [19]
Iritani et al.

[11] Patent Number: 5,622,859
[45] Date of Patent: Apr. 22, 1997

[54] BIOLOGICALLY PURE STRAIN OF *ENTEROCOCCUS FALCIUM* FERM BP-4504

[75] Inventors: Satoshi Iritani, Akawa-gun; Masakazu Mitsuhashi, Okayama; Hiroto Chaen, Okayama; Toshio Miyake, Okayama, all of Japan

[73] Assignee: Kabushiki Kaisha Hayashibara Seibutsu Kagaku Kenkyujo, Okayama, Japan

[21] Appl. No.: 623,007

[22] Filed: Mar. 28, 1996

Related U.S. Application Data

[63] Continuation of Ser. No. 364,489, Dec. 27, 1994, Pat. No. 5,545,418.

[30] Foreign Application Priority Data

Dec. 27, 1993 [JP] Japan ..................... 5-346818

[51] Int. Cl.$^6$ ............. A01N 63/00; C12N 1/00; C12N 1/12; C12N 1/20
[52] U.S. Cl. ................ 435/252.1; 424/93.48; 426/53; 435/822
[58] Field of Search ............ 424/93.48; 426/53; 435/252.1, 822

[56] References Cited

U.S. PATENT DOCUMENTS

| | | | |
|---|---|---|---|
| 3,903,307 | 9/1975 | Kimura | 426/53 |
| 4,087,317 | 5/1978 | Roberts | 162/23 |
| 4,451,567 | 5/1984 | Ishibashi et al. | 435/170 |
| 4,526,791 | 7/1985 | Young | 426/53 |

FOREIGN PATENT DOCUMENTS

| | | |
|---|---|---|
| 5239457 | 9/1993 | Japan . |
| 286211 | 11/1928 | United Kingdom . |
| 1571855 | 7/1977 | United Kingdom . |
| 8001351 | 7/1980 | WIPO . |
| 9403646 | 2/1994 | WIPO . |

OTHER PUBLICATIONS

Dietary Fiber, pp. 38–46, 1985.
Hasegawa; Biseibutsu no Bunrui to Doutei (Classification and Identification of Microorganisms), 1985.
Sneath et al; Bergey's Manual of Systematic Bacteriology; vol. 2; 1986.
Molina et al; *Nutritive Value for Ruminants of Sugar Cane Bagasse Ensiled After Spray Treatment with Different Levels;* Animal Feed Science and Technology; vol. 9; pp. 1–7; 1983.
Playne; *Increased Digestibility of Bagasse by Pretreatment with Alkalis an Steam Explosion;* Biotechnology and Bioengineering; vol. XXVI; pp. 426–433; 1984.
Kato et al., "Isolation of Enterococcus faecium with Antibacterial Activity and Characterization of Its Bacteriocin", *Biosci. Biotech. Biochem.*, 57(4), 551–556, 1993.
Efthymiou et al., "Development of a Selective Enterococcus Medium Based on Manganese Ion Deficiency, Sodium Azide, and Alkaline pH," *Applied Microbiology*, vol. 28(3), pp. 411–416, 1974.

*Primary Examiner*—John W. Rollins
*Assistant Examiner*—Deborah K. Ware
*Attorney, Agent, or Firm*—Browdy and Neimark

[57] ABSTRACT

Disclosed is an alkali-treated bagasse prepared by softening a bagasse with calcium oxide together with or without sodium hydroxide while preventing the substantial decomposition of cellulose and hemicellulose, a bagasse feed and a fermented bagasse feed prepared from the alkali-treated bagasse, and their preparations and uses as well as bacteria for fermenting the alkali-treated bagasse. These bagasse and bagasse feeds save sugar-refinery industries from the difficulties to treat bagasse deemed as an unutilized industrial waste, and livestock farming industries from the shortage of roughage, and further is extremely significant in agriculture, industries of sweetening products, feed industries and livestock product processors. A bacterium strain particularly useful for the fermentation is *Enterococcus faecium* FERM BP-4504.

1 Claim, No Drawings

BIOLOGICALLY PURE STRAIN OF *ENTEROCOCCUS FALCIUM* FERM BP-4504

This is a continuation of parent application Ser. No. 08/364,489 filed Dec. 27, 1994, now U.S. Pat. No. 5,548,418.

BACKGROUND OF THE INVENTION

1. Field of the Invention

The present invention relates to an alkali-treated bagasse and its preparation and uses, more particularly to an alkali-treated bagasse whose structure is softened while preventing the decomposition of cellulose and hemicellulose, and a bagasse feed and a fermented bagasse feed prepared from said alkali-treated bagasse, as well as to their preparation and uses, and to a microorganism utilizable for fermenting said alkali-treated bagasse.

2. Description of the Prior Art

Although having been utilized in part as a fuel source, bagasse is a squeezed waste of sugar cane which contains a vast of cellulose and hemicellulose for which there have not yet been found other useful applications. The problem is that more than 100 million tons of bagasse produced annually worldwide have been still unutilized.

On the other hand, livestock fed with grass, or ruminants like cattle and sheep assimilate cellulose and hemicellulose of plants in nature, differerently from monogastric animals like human beings, pigs and poultry, and further physiologically utilize said cellulose and hemicellulose as an energy source.

Recently, the consumption of livestock products such as beef and dairy products has been increased so that an intensive livestock farming system has been remarkably developed to breed a lot of cattle standing in the same direction together in a small shed, and said intensive livestock farming system has tightened the supply of feed grass required for breeding and also has led the rapid increase of the demand for roughage containing cellulose and hemicellulose substitutable for feed grass.

There have been many studies to utilize bagasse as roughage for a long time, however, in addition of cellulose and hemicellulose, bagasse contains a considerable amount of lignin having a tight linkage with fibre like cellulose and said linkage tightens the structure of bagasse in the same manner as bamboo. While ruminants can assimilate bagasse itself, the digestibility of bagasse for ruminants is relatively low and the taste and nutrient value of bagasse for ruminants is very unpreferable. It is known that, when cattle assimilate a raw bagasse, there is a danger that pieces of said bagasse could be stuck into the walls of cattle's rumen.

For improving a nutrient value of bagasse, there were many proposals of increasing the digestibility of bagasse by decomposing lignin to soften the structure of bagasse. Most of said proposals comprise treating bagasse with an alkaline reagent and succeedingly fermenting the resultant alkali-treated bagasse. In such alkali treatment, as described in *Biotechnology and Bioengineering*, volume 26, pp. 426–433 (1984), it is known to use as an alkaline reagent sodium hydroxide and calcium hydroxide as well as sodium carbonate. In the fermentation of an alkali-treated bagasse, for instance, as described in *Animal Feed Science and Technology*, volume 9, pp. 1–17 (1983), an ensilage of an alkali-treated bagasse with sodium hydroxide is known.

We eagerly studied these conventional methods and found that in the case of an alkali treatment with sodium hydroxide, because of its strong alkalinity, a relatively small amount of sodium hydroxide was required to raise the pH of bagasse mixtures to a relatively-high level so that lignin was readily decomposed to soften the structure of bagasse without readily decomposing cellulose and hemicellulose necessary for roughage. In addition, it was found that the pH level of alkali-treated bagasse was decreased, specifically, said pH level was decreased very gradually over a long period of time to the range wherein lactic acid bacteria were proliferative, and further that a long period of 25 to 90 days was required for preparing a fermented bagasse feed from said alkali-treated bagasse. It was found that, in order to avoid said disadvantage and to increase rapidly the pH level of alkali-treated bagasse, said alkali-treated bagasse should be neutralized with an acid solution and there were many other drawbacks in conventional methods.

It was found that in the case of using calcium hydroxide and sodium carbonate, because of their relatively weak alkalinity, the amounts of alkaline reagents used was increased to the level of about 12 to 30 w/w % of the bagasse, d.s.b. (the wording of "w/w %" as referred to the invention will be abbreviated as "%" hereinafter), the cost of alkali treatment was raised and ruminants consuming excessively alkaline reagents desired a large amount of water so that they excreted a large amount of urine. Therefore it was found that the conventional alkali treatment has an extreme drawback by adversely physiologically affecting ruminants.

SUMMARY OF THE INVENTION

The present invention provides an alkali-treated bagasse which overcomes the above drawbacks and its uses, and considering a vast of demands for said bagasse, the present invention provides a preparation of said bagasse readily at a relatively-low cost and in a relatively-short period.

We, in order to overcome the above object, have studied eagerly the use of to an alkaline reagent in treatment of bagasse. As a result, we unexpectedly found that calcium oxide which has not been considered conventionally is suitable for the production of an alkali-treated bagasse and also preferable for the preparation of a fermented bagasse feed from said alkali-treated bagasse, and accomplished the present invention.

Furthermore, we found that using as alkaline reagents sodium hydroxide together with calcium oxide is far more suitable than and in no way inferior to using only calcium oxide and further is preferable for the preparation of an alkali-treated bagasse as well as a fermented bagasse feed using said alkali-treated bagasse, and accomplished the present invention.

DETAILED DESCRIPTION OF THE INVENTION

The present invention utilizing calcium oxide together with or without sodium hydroxide as alkaline reagents for an alkali-treatment of bagasse has the following characteristics (1) producing an alkali-treated bagasse in which the structure is softened without almost decomposing cellulose and hemicellulose as an effective component of bagasse; (2) attaining the object of an alkali-treatment by using a relatively-small amount of an alkaline reagent in a relatively-short period because calcium oxide is an active alkaline reagent or absorbs water and is exothermic enough to promote alkali reaction; (3) inoculating a seed culture of a lactic acid bacterium in an early stage without neutralization by acid because the pH level of an alkali-treated bagasse is decreased relatively rapidly; (4) suitable for a large-scale production of an alkali-treated bagasse and a fermented bagasse feed using said alkali-treated bagasse because of easily controllable, short-period and relatively low cost production; (5) preferable nutritionally for ruminants because a relatively-small amount of alkaline reagents relative to bagasse is used without considering the excess intake of alkaline reagents and because the nutritive value of bagasse is intensified by adding thereto an appropriate amount of calcium or minerals; and further (6) a fermented bagasse feed obtainable by the present invention has a relatively-high quality and excellent digestibility and good taste, and (7) an alkali-treated bagasse obtained and a bagasse feed as well as a fermented bagasse feed prepared from said alkali-treated bagasse is usable preferably as a livestock feed as well as an organic fertilizer.

The present invention is explained in detail as follows:

A bagasse usable in the present invention includes those having a water content of about 40 to 50% as produced in sugar refineries. However, if necessary, a dried and stored bagasse is usable. A preferable water content for use in an alkali-treatment is in the range from the lower limit wherein both bagasse and alkaline reagents could be mixed sufficiently to the upper limit wherein an alkali solution is prevented from leaking out of an alkali-treated bagasse. Specifically, a water content of about 40 to 90%, although that of about 45 to 80% is more suitable.

As to the calcium oxide usable in the present invention, those having a higher activity, namely, those as much water as possible are desirable, which can be in the form of granules or powder, if necessary. The amount of calcium oxide suitably used in the invention is in the range of not exceeding 5% with respect to bagasse, preferably, in the range of 2 to 4%, on a dry solid basis (d.s.b.). The amount of sodium hydroxide suitably used in the invention is in the range of not exceeding the amount of the calcium oxide, preferably, not more than 3%.

In the case of adding alkaline reagents to a bagasse under the coexistence of water, any method of mixing alkaline reagents with the bagasse containing a certain amount of water can be favorably employed, for example, at first, bagasse is macerated and succeedingly mixed with alkaline reagents, or vice versa ad libitum. These procedures can be conducted at an ambient temperature, usually, a temperature in the range of about 10° to 35° C.

The initial pH level of the bagasse thus obtained is usually not less than about pH 10.3, favorably, in the range of about pH 10.5 to 12, and by allowing said bagasse to stand at an ambient temperature, an alkali-treated bagasse having not more than pH 10, preferably, not more than pH 9.5 is readily obtainable, and thus the object of alkali-treatment is attained in a short time of about 10 to 40 hours.

The alkali-treated bagasse thus obtained is softened without substantially damaging cellulose and hemicellulose, particularly, in the case of using calcium oxide together with sodium hydroxide, in comparison of the single use of calcium oxide, the lignin of the alkali-treated bagasse is decomposed to soften further its structure without substantially damaging cellulose and hemicellulose, and is a suitable raw material of a fermented bagasse feed. The alkali-treated bagasse can be advantageously used, without fermentation, as various feed by mixing it with such nutrients as an energy source like molasses and organic acid and protein like a de-fatted soybean and a cottonseed lees.

We found that the alkali-treated bagasse or a bagasse feed obtainable by blending said alkali-treated bagasse with various nutrients is suitable as an organic fertilizer which is appropriately decomposed in soil and exhibits remarkably its ability of providing a nutrient supplement to soil and of improving conditions as well as humidity of soil. In case that the alkali-treated bagasse or the bagasse feed is utilized as a fertilizer, a relatively-small amount of the bagasse or the feed, usually acres selected from the range of about 40 to 500 kg in 10, can be scattered in soil, which is variable depending on the composition of the bagasse or the feed, conditions of soil and the kind of crops to be grown.

For the purpose of preparing a fermented bagasse feed from an alkali-treated bagasse, the alkali-treated bagasse is fermented naturally, preferably, by adding a seed culture of lactic acid bacteria and nutrients to the alkali-treated bagasse and then fermenting the mixture after or immediately before the pH level of the alkali-treated bagasse decreases to a pH range wherein a seed culture of lactic acid bacteria proliferates. In such a case, if necessary, an alkali-treated bagasse can be partially neutralized with an acid solution to meet the minimum pH level for the proliferation of lactic acid bacteria inoculated.

The lactic acid bacteria usable in the present invention include those capable of fermenting in a medium containing an alkali-treated bagasse, for instance, those of the genera Enterococcus, Lactobacillus, Streptococcus and Pediococcus are preferable. Specifically, *Enterococcus faecium* HL-5 (FERM BP-4504) belonging to the genus Enterococcus newly isolated by the present inventors, which proliferates in alkali solutions of not less than pH 9.5 or in high concentration saline solutions containing 6.5% sodium chloride and further produce lactic acid to decrease the pH of the alkali-treated bagasse, is suitable for preparing a fermented bagasse which is preferred.

We found that the present microorganism is capable of proliferating in alkaline nutrient media of pH not more than 10 containing an alkali-treated bagasse, desirably, those having a pH not less than 9 to a pH not more than 10, more desirably, not less than 9.5 to a pH not more than 10, and said microorganism can be seeded at a relatively early stage wherein the pH decrease of alkali-treated bagasse is close to pH 10, in other words, a desirable alkali treatment period can be usually 1 to 2 days or less. Furthermore the microorganism is characterized in that it satisfactorily shortens the preparation period of a fermented bagasse feed to about 3 to 6 days. When inoculated into the above alkali-treated bagasse with calcium oxide whose pH level readily decreases, the microorganism advantageously shortens the production period of fermented bagasse feeds.

The results of identification study of the microorganism, the genera Enterococcus HL-5 newly isolated from ensiled corns by the present inventors, are shown as follows. The identification study was conducted according to *Biseibutsu no Bunrui to Doutei* (Classification and Identification of Microorganism)(Edited by Hasegawa, Gakujyutsu Shutsupan Center, 1985).

[A. Morphology]
(1) Characteristics of cells when incubated at 37° C. in MRS agar
Usually existing in a coccus form of 0.9 to 1.2 μm;
Existing in a coupled- or short linked-form;
Motility: Negative;
Asporogenicity; and
Gram stain: Positive.
(2) Characteristics of cells when incubated at 37° C. in PG agar
Usually existing in a coccus form of 0.9 to 1.2 μm;

Existing in a coupled- or short linked-form;
Motility: Negative
Asporogenicity; and
Gram stain: Positive.

[B. Cultural properties]

(1) Characteristics of colony formed when incubated at 37° C. in MRS agar plate
Shape: Circular colony having a diameter of about 1 to 2 mm after 3 days incubation;
Rim: Entire;
Projection: Hemispherical shape;
Gloss: Wet-look gloss;
Surface: Smooth; and
Color: Milk white and semitransparent.

(2) Not liquefying MRS gelatin when stab cultured at 37° C.

(3) Forming acid and gelatinizing litmus milk when incubated therein at 37° C.

[C. Physiological properties]

(1) Catalase: Negative
(2) Oxidase: Negative
(3) Liquefaction of gelatin: Negative
(4) Hydrolysis of casein: Negative
(5) Hydrolysis of arginine: Positive
(6) Tolerance to 40% bile: Positive
(7) Hemolysis: Negative
(8) Hydrolysis of hippurate: Positive
(9) Hydrolysis of aesculin: Positive
(10) Growth at 10° to 45° C.: Positive
(11) Growth at pH 9.6: Positive
(12) Growth in 6.5% NaCl: Positive
(13) Oxygen requirements: Facultative an anaerobic
(14) Acid formation from carbon source
Amygdalin: Positive
Arabinose: Positive
Cellobiose: Positive
Aesculin: Positive
Fructose: Positive
Galactose: Positive
Glucose: Positive
Gluconic acid: Positive
Lactose: Positive
Maltose: Positive
Mannitol: Positive
Mannose: Positive
Melezitose: Negative
Melibiose: Positive
Raffinose: Positive
Rhamnose: Positive
Ribose: Positive
Salicin: Positive
Sorbitol: Negative
Sucrose: Positive
Trehalose: Positive
Xylose: Negative
Arbutin: Positive
Sorbose: Negative

(15) Main diamino acids of cell walls: Lysine

(16) Mol % glycine (G) plus cytosine (C): 38.6%

The above bacteriological properties were compared with those of known strains with reference to *Bergey's Manual of Systematic Bacteriology*, volume 2 (1986). As a result, based on the above properties, it was revealed that the microorganism was identified with a microorganism of the species of *Enterococcus faecium* except for the property that acid formation from sorbose was negative.

On the basis of the above result, the present inventors designated the microorganism as a novel microorganism *Enterococcus faecium* HL-5 and, on the date of Dec. 17, 1993, deposited it in the National Institute of Bioscience and Human-Technology Agency of Industrial Science and Technology placed at 1-3, Higashi 1 chome Tsukuba-shi Ibaraki-ken, and it was accepted under the deposit number of FERM BP-4504. In the present invention, in addition to the above microorganism, the other strains belonging to the genus Enterococcus, which are capable of proliferating in an alkali medium having a pH not less than 9.5 and containing an alkali-treated bagasse, and also their mutants are utilizable preferably. The other strains belonging to the genus Enterococcus usable in the present invention include, for instance, *Enterococcus casseliflavus* IFO 3531, *Enterococcus durans* IFO 13131, *Enterococcus faecalis* IFO 3791, *Enterococcus faecium* IFO 3535 and *Enterococcus hirae* IFO 3181T.

It was found that, similarly to *Enterococcus faecium* HL-5 isolated by the present inventors, lactic acid bacteria belonging to the genera Enterococcus are capable of proliferating in a relatively early stage of the pH decrease of alkali-treated bagasse, specifically, not less than pH 9, desirably, capable of proliferating sufficiently in the stage of not less than pH 9.5, and realize an early stage inoculation, and therefore the lactic acid bacteria are suitable for shortening the fermentation period.

The combination use of a lactic acid bacterium belonging to the genus Enterococcus and one or more members selected from lactic acid bacteria belonging to the genera Lactobacillus, Pediococcus and Streptococcus which are capable of proliferating at a pH of less than and closer to 8 is extremely desirable for the production of a high-quality fermented bagasse feed having an excellent feed taste wherein the production period is shortened.

The strains belonging to the genera Lactobacillus include, for instance, *Lactobacillus rhamnosus* IFO 3532, *Lactobacillus plantarum* IFO 3070, *Lactobacillus sake* IFO 3541, *Lactobacillus acidophilus* IFO 13952, *Lactobacillus helveticus* IFO 3809 and *Lactobacillus brevis* IFO 3345, and the combination use of one or more members of said strains are suitable for improving the preference of fermented bagasse feeds.

Furthermore, microorganisms belonging to the genera Pediococcus and Streptococcus, for instance, *Pediococcus acid ilactici* IFO 3076 and *Streptococcus bovis* IFO 12057 are utilizable advantageously.

An alkali-treated bagasse can be fermented by incorporating a seed culture of lactic acid bacteria and nutrients into the alkali-treated bagasse, usually, by adding nutrients, if necessary, together with an appropriate amount of water to said alkali-treated bagasse, inoculating a seed culture of lactic acid bacteria and then fermenting the mixture at an ambient temperature, desirably, in the range of about 15° to 50° C., for instance, such a fermentation can be effected by fermenting anaerobically for about 2 or 4 days the above mixture contained in a flexible bag or lapped.

The nutrients usable in the invention include nutrients useful for the proliferation of lactic acid bacteria and/or for animals assimilating the fermented bagasse feed obtainable by the present invention, usually, one or more members of the group consisting of energy sources, protein, minerals and vitamins can be used. Specifically, for instance, molasses, sugar, dextrose, starch, organic acids, alcohols, press-ground grain, sorghum, barley, barley, pulverized rice, rice bran, wheat flour, wheat flour bran, corn, corn gluten, feed in general, de-fatted soybean, soybean casein, cottonseeds, cottonseed lees, rape seed lees, beer lees, milk, de-fatted dry milk, milk casein, milk serum, blood meal, bone meal, feather meal, fish meal, urea, ammonium salts, calcium salts, magnesium salts, sodium salts, phosphates, iron salts, copper salts, zinc salts, water-soluble vitamins and lipid-soluble vitamins are used arbitrarily.

Preferably, the above nutrients are incorporated usually in the range of not exceeding the amount of used bagasse, d.s.b. The wording of "incorporating an appropriate amount of water" as referred to the present invention means to incorporate the water into the contents in the range from the lower limit proceeding lactic acid fermentation to the upper limit preventing nutrient solutions from leaking out of the resultant fermented bagasse feed, usually in the range of about 40 to 90%, desirably about 45 to 80%, and in the case of putting priority on preservation of the fermented bagasse feed, the water content of about 45 to 60% is suitable. The kind and amount of nutrients used in the fermentation can be selected arbitrarily depending on the final products, for instance, roughage or well-balanced feed containing nutrients proportionately. The fermented bagasse feeds thus obtained are acidified by lactic acid and are excellent in preservation and taste, although these properties are variable dependently on the kind and amount of used nutrients. If necessary, it is feasible advantageously that in order to improve the preservation of said fermented bagasse feeds, they are dried by air or hot air to give a water content of not more than 40%, preferably, to decrease said water content to not more than 30% and then the fermented bagasse feeds dried thus are readily preserved and utilized.

The fermented bagasse feeds thus obtained in the present invention are high-quality feeds having good taste and excellent digestibility. The fermented bagasse feeds are utilizable mainly as a feed for ruminants, and if necessary, for monogastric animals like pigs and poultry, specifically said bagasse feeds are usable as a feed which is capable of controlling and improving intestinal conditions and of preventing infections. Usually cattle assimilate the present fermented feed of about 4 to 10 kg or more in a day, and the cattle increase their body weights by not less than about 2 kg/body in a day, preferably, not less than about 2.5 kg/body, depending on the kind of fermented bagasse feeds and the ages of the cattle.

It is feasible advantageously that, depending on the kind of animals to be fed and their ages, a fermented bagasse feed can be arbitrarily mixed other nutrients.

We found that the bagasse feed is usable preferably as organic fertilizer appropriately decomposed in soil and exhibits remarkably its ability of providing a nutrient supplement to soil and of improving conditions as well as humidity of soil. In case that the bagasse feed is utilized as a fertilizer, a relatively-small amount of the bagasse feed, usually selected from the range of about 60 to 800 kg in 10 acres, can be scattered in soil, which is variable depending on the composition of the bagasse or the feed, conditions of soil and the kind of crops to be grown.

The following experiments explain the present alkali treatment using calcium oxide in detail:

Experiment 1
Effect of alkaline reagent on the preparation of alkali-treated bagasse Bagasse was macerated with water to give a water content of 70% and mixed with as an alkaline reagent 3, 5 or 7% sodium hydroxide (NaOH) to bagasse, d.s.b., respectively and 2, 3, 5, or 7% calcium oxide (CaO) to bagasse, d.s.b., respectively as uniformly as possible, and the mixture was allowed to stand at ambient temperature. The alkali-treated bagasse thus obtained was analyzed for its changes of pH and components as well as its structural flexibility.

The pH level of the alkali-treated bagasse was determined immediately after the mixing and at 24 and 48 hours termination. The samples were analyzed by admixing 1 part by weight of an alkali-treated bagasse specimen with 2 parts by weight of refined water, allowing the mixture to stand for 10 minutes, filtering the mixture, and measuring the pH of the resultant filtrated on a pH meter. As to components, raw bagasse and the alkali-treated bagasse collected at 24 and 48 hours termination were respectively divided into 8 samples, and their contents of hemicellulose, cellulose and lignin were determined and their average value calculated.

The above measurement was conducted in accordance with the Van Soest's detergent filter method as described in the 3.1 chapter of "Dietary Fiber", pp. 38 to 46 (1982), published by Dai-ichi Shutupan Co., Ltd., Tokyo, Japan. The components of raw bagasse essentially consisted of 28.7% hemicellulose, 52.6% cellulose and 11.9% lignin, d.s.b.

The structural flexibility of the alkali-treated bagasse was analyzed by studying its touch as clutched by hands wearing thin rubber gloves. The results were tabulated in Table 1.

In Table 1, numerical values pertaining to the item of hemicellulose, cellulose and lignin are designated as a ratio of the remaining hemicellulose, cellulose and lignin after alkali treatment as compared to their initial contents in raw bagasse respectively.

As shown in Table 1, sodium hydroxide used conventionally tends to decrease the pH slowly in comparison with calcium oxide. As to the change of components of bagasse, it was revealed that cellulose and hemicellulose important for roughage are remarkably decomposed and spoiled by sodium hydroxide treatment.

On the contrary, it was found that the present alkali-treated bagasse with calcium oxide, free of substantial decomposition of cellulose and hemicellulose, is advantageously used for a raw material of feeds.

Furthermore the alkali-treated bagasse with calcium oxide, which decreases its pH level relatively rapidly to the range wherein lactic acid bacteria for the production of fermented bagasse feeds proliferated and making it possible to inoculate into the bagasse lactic acid bacteria at a relatively early stage, is preferably suitable for a raw material of fermented bagasse feeds.

Experiment 2
Effect of the combination of calcium oxide and sodium hydroxide on alkali-treated bagasse In accordance with the method of Experiment 1, bagasse was macerated to give a water content of 70%, the macerated

TABLE 1

| | | Time (hr) | | | | | | | | | |
|---|---|---|---|---|---|---|---|---|---|---|---|
| | | 0 | 24 | | | | | 48 | | | |
| | | pH | pH | HC | C | L | F | pH | HC | C | L | F |

Control

| Alkali | (%) | | | | | | | | | | | |
|---|---|---|---|---|---|---|---|---|---|---|---|---|
| NaOH | 3 | 10.8 | 10.3 | 79.4 | 93.5 | 75.3 | Good | 10.0 | 72.3 | 91.5 | 74.5 | Good |
| | 5 | 11.3 | 10.7 | 65.7 | 88.2 | 72.8 | Good | 10.3 | 59.8 | 85.4 | 71.4 | Good |
| | 7 | 12.4 | 11.5 | 53.6 | 81.3 | 66.4 | Good | 11.0 | 37.7 | 78.6 | 54.6 | Good |

The present invention

| CaO | 2 | 10.4 | 8.9 | 99.2 | 99.3 | 82.2 | Good | 8.5 | 99.1 | 99.2 | 80.2 | Good |
|---|---|---|---|---|---|---|---|---|---|---|---|---|
| | 3 | 10.7 | 9.3 | 98.1 | 99.5 | 80.6 | Good | 8.7 | 98.0 | 98.1 | 79.0 | Good |
| | 5 | 11.2 | 10.4 | 97.4 | 97.4 | 77.5 | Good | 10.0 | 96.1 | 97.3 | 75.6 | Good |
| | 7 | 11.9 | 11.2 | 91.6 | 94.8 | 75.2 | Good | 10.5 | 90.3 | 93.6 | 74.4 | Good |

HC: hemicellulose, C: cellullose, L: lignin, and F: flexibility
*Numerical values (%) pertaining to hemicellulose, cellulose and lignin mean the ratios of the remaing hemicellulose, cellulose and lignin as compared to their initial contents in raw bagasse.

bagasse was mixed 2 or 3% calcium oxide (CaO), and 1, 2 or 4% sodium hydroxide (NaOH) with respect to bagasse, d.s.b., respectively, and the alkali-treated bagasse thus obtained was studied for its changes of pH and components as well as its structural flexibility. The results were tabulated in Table 2.

As shown in Table 2, it was unexpectedly found that the use of a combination of calcium oxide and sodium hydroxide as alkaline reagents provided the similar advantageous result as Experiment 1 using only calcium oxide. In other words, each sample of alkali-treated bagasse in Experiment 2 was sufficiently flexible without decomposing cellulose and hemicellulose similarly as in the case of using only calcium oxide, and it was revealed that the use of a combination of calcium oxide and sodium hydroxide is advantageous.

Specifically, it was revealed that incorporating sodium hydroxide in the range of not exceeding the amount of calcium oxide used allows the effective components of cellulose and hemicellulose in a bagasse to remain sufficiently intact and also to decompose, lignin and the bagasse thus alkali-treated is flexible sufficiently and suitable for an alkali-treated bagasse.

The following examples A illustrate the preparations of an alkali-treated bagasse. Examples B illustrate the uses of a fermented bagasse feed in detail, but are by no means limitative of the present invention:

Example A-1

Bagasse was macerated to give a water content of 70% and the resultant macerated bagasse was added with 4% calcium oxide to bagasse, d.s.b., as alkaline reagents and

TABLE 2

| Alkali (%) | | | | Time (hr) | | | | | | | | |
|---|---|---|---|---|---|---|---|---|---|---|---|---|
| | | 0 | 24 | | | | | 48 | | | | |
| CaO | NaOH | pH | pH | HC | C | L | F | pH | HC | C | L | F |
| 2 | 1 | 10.8 | 9.4 | 94.4 | 99.5 | 79.7 | Good | 9.0 | 98.5 | 99.1 | 78.3 | Good |
| 2 | 2 | 11.1 | 10.3 | 99.1 | 99.3 | 77.0 | Good | 9.6 | 98.2 | 98.4 | 75.0 | Good |
| 2 | 4 | 12.0 | 11.3 | 78.6 | 95.4 | 73.4 | Good | 10.4 | 76.6 | 93.5 | 70.2 | Good |
| 3 | 1 | 11.0 | 10.1 | 98.5 | 99.3 | 77.4 | Good | 9.1 | 97.2 | 99.2 | 76.2 | Good |
| 3 | 2 | 11.6 | 10.4 | 98.2 | 98.1 | 75.0 | Good | 9.7 | 97.1 | 99.1 | 74.3 | Good |
| 3 | 4 | 12.0 | 11.3 | 74.6 | 92.4 | 72.2 | Good | 10.4 | 72.5 | 90.2 | 68.7 | Good |

HC: hemicellulose, C: cellullose, L: lignin, and F: flexibility
*Numerical values (%) pertaining to hemicellulose, cellulose and lignin mean the ratios of the remaing hemicellulose, cellulose and lignin as compared to their initial contents in raw bagasse.

allowed to stand overnight to obtain an alkali-treated bagasse having pH about 9.7.

The present bagasse is usable as a raw material for fermented bagasse feeds or preferably utilizable without fermentation as a roughage for formula feeds.

Example A-2

Bagasse was macerated to give a water content of 60%, and the resultant macerated bagasse was mixed with as alkaline reagents 3% calcium oxide and 1% sodium hydroxide to bagasse, d.s.b., respectively, and the mixture was allowed to stand overnight to obtain an alkali-treated bagasse having pH about 10.2.

Similarly as the product in Example A-1, the product is usable as a raw material for fermented bagasse feeds or preferably utilizable as a roughage for formula feeds.

Example A-3

Bagasse having a water content of about 47% was mixed with as alkaline reagents 3% calcium oxide and 2% sodium hydroxide to bagasse, d.s.b., respectively, and the mixture was allowed to stand overnight to obtain an alkali-treated bagasse having about pH 9.6.

Similarly as the product in Example A-1, the product is usable as a raw material for fermented bagasse feeds or preferably utilizable as a roughage for formula feeds.

Example A-4

Bagasse having a water content of about 45% was mixed with as alkaline reagents 2% calcium oxide and 2% sodium hydroxide to bagasse, d.s.b., respectively, and the mixture was allowed to stand overnight to obtain an alkali-treated feed bagasse having pH about 10.3.

Similarly as in Example A-1, the product is usable as a raw material for fermented bagasse feeds or preferably utilizable as a roughage for formula feeds.

Example B-1

A seed culture of *Enterococcus faecium* FERM BP-4504 was inoculated into a nutrient culture medium containing 100 parts by weight of an alkali-treated bagasse obtained by the method in Example A-1, 10 parts by weight of molasses, 0.2 parts by weight of urea and 0.2 parts by weight of salt as nutrients, and the mixture was covered with a plastic sheet and fermented at a room temperature for 2 days to obtain a fermented bagasse feed.

The fermented bagasse feed, sufficiently digestible, is preferably suitable as a high-quality feed having an excellent taste for ruminants. It is advantageously feasible to increase the feed value of the fermented bagasse feed and to produce a feed for monogastric animals like pigs and poultry by blending other nutrients with the fermented bagasse feed.

Example B-2

Seed cultures of *Enterococcus casseliflavus* IFO 3531 and *Lactobacillus plantarum* IFO 3070 were inoculated into a nutrient culture medium containing 100 parts by weight of an alkali-treated bagasse obtained by the method in Example A-2 and as nutrients 20 parts by weight of wheat flour bran, 10 parts by weight of molasses, 0.2 parts by weight of ammonium phosphates and 40 parts by weight of water, the mixture was fermented similarly as in Example B-1 to obtain a fermented bagasse feed.

The fermented bagasse feed, sufficiently digestible, is preferably suitable as a high-quality feed having an excellent taste for ruminants. It is advantageously feasible to increase the feed value of the fermented bagasse feed and to produce a feed for monogastric animals like pigs and poultry by blending other nutrients with the fermented bagasse feed.

Example B-3

Seed cultures of *Enterococcus faecalis* IFO 3791 and *Lactobacillus brevis* IFO 3345 were inoculated into a nutrient culture medium containing 100 parts by weight of an alkali-treated bagasse obtained by the method in Example A-3 and as nutrients 10 parts by weight of wheat flour bran, 10 parts by weight of de-fatted soybean, 5 parts by weight of corn meal, 10 parts by weight of molasses, 0.2 parts by weight of ammonium phosphate and 60 parts by weight of water, the mixture was fermented in a flexible bag at a room temperature for 2 days to obtain a fermented bagasse feed.

The fermented bagasse feed, sufficiently digestible, is preferably suitable as a high-quality feed having an excellent taste for ruminants. It is advantageously feasible to increase the feed value of the fermented bagasse feed and to produce a feed for monogastric animals like pigs and poultry by blending other nutrients with the fermented bagasse feed.

Example B-4

Seed cultures of *Enterococcus faecium* FERM BP-4504, *Lactobacillus rhamnosus* IFO 3532 and *Lactobacillus acidophilus* IFO 13952 were inoculated into a nutrient culture medium containing 100 parts by weight of an alkali-treated bagasse obtained by the method in Example A-4 and as nutrients 20 parts by weight of wheat flour bran, 5 parts by weight of press-ground barley, 5 parts by weight of rice bran, 10 parts by weight of molasses, 5 parts by weight of milk serum and 70 parts by weight of water, the mixture was fermented in a flexible bag at a room temperature for 3 days to obtain a fermented bagasse feed.

The fermented bagasse feed, sufficiently digestible, is preferably suitable as a high-quality feed having an excellent taste for ruminants. It is advantageously feasible to increase the feed value of the fermented bagasse feed to produce a feed for monogastric animals like pigs and poultry by blending other nutrients with the fermented bagasse feed.

Example B-5

A fermented and dried bagasse feed was prepared by drying in hot air a fermented bagasse feed prepared by the method in Example B-3 to obtain a dried and fermented bagasse feed having a water content of 20%.

The bagasse feed, a high quality feed having sufficient digestibility, good taste and excellent in preservation, is suitable for long-distance transportation.

Example B-6

One hundred parts by weight of an alkali-treated bagasse obtained by the method in Example A-3 was blended uniformly with as nutrients 10 parts by weight of wheat flour bran, 10 parts by weight of de-fatted soybean, 2 parts by weight of cottonseeds, 5 parts by weight of molasses, 1 part by weight of lactic acid and 40 parts by weight of water, and then the bagasse feed was obtained.

The bagasse feed, a high quality feed having sufficient digestibility and good taste, is suitable for ruminants.

Example B-7

Twenty cattle having a body weight of 400 to 500 kg were fed for a period of 60 days by providing them with the fermented bagasse feed obtained by the method in Example B-3. The taste of the fermented bagasse feed is very preferable for the cattle and their average intake of the fermented bagasse feed in a day was about 20 to 25 kg/body, and further they increased their body weights by about 2.1 kg/body in a day on an average in satisfactory physical and feeding conditions.

As described above, bagasse, an unutilized agricultural waste, is utilized according to the invention to prepare an alkali-treated bagasse without decomposing cellulose and hemicellulose as an effective component by using as alkaline reagents calcium oxide together with or without sodium hydroxide, and further a good taste and high quality fermented bagasse feed is produced easily within a relatively-short period of time by inoculating lactic acid bacteria to the alkali-treated bagasse and succeedingly fermenting the mixture.

It was found that the alkali-treated bagasse thus obtained and a bagasse feed as well as a fermented bagasse feed is usable as a feed for livestock as well as advantageously utilizable as an organic fertilizer.

Accordingly, the present invention saves sugar-refinery industries from the difficulties of treating bagasse deemed as an unutilized industrial waste and livestock farming industries from the shortage of roughage, and further is extremely significant in agriculture, industries of sweetening products, feed industries and livestock product processors. Furthermore, in the case of standing in global view of observing the earth overall, it is no exaggeration to say that the present invention established a novel technology to save our future facing an environmental disruption, an overflowing population and a food crisis by providing a vast amount of foodstuff like livestock and milk products from bagasse or unutilized biomass exhausted largely and annually, without any competition with our foods.

While there has been described what is at present considered to be the preferred embodiments of the invention, it will be understood the various modifications may be made therein, and it is intended to cover in the appended claims all such modifications as fall within the true spirits and scope of the invention.

We claim:

1. A biologically pure *Enterococcus faecium* FERM BP-4504, which is a bacterium capable of proliferating in an alkaline nutrient culture medium having a pH not less than 9.5.

* * * * *